United States Patent
Kimata et al.

(10) Patent No.: US 6,813,930 B2
(45) Date of Patent: Nov. 9, 2004

(54) GAS SENSOR

(75) Inventors: Takehito Kimata, Ichinomiya (JP); Masato Ozawa, Toyota (JP)

(73) Assignee: Denso Corporation, Aichi-Pref. (JP)

( * ) Notice: Subject to any disclaimer, the term of this patent is extended or adjusted under 35 U.S.C. 154(b) by 0 days.

(21) Appl. No.: 09/885,023

(22) Filed: Jun. 21, 2001

(65) Prior Publication Data

US 2002/0000116 A1 Jan. 3, 2002

(30) Foreign Application Priority Data

Jun. 30, 2000 (JP) .................................. 2000-198431
Apr. 18, 2001 (JP) .................................. 2001-119996

(51) Int. Cl.[7] .............................................. G01N 7/00
(52) U.S. Cl. ..................... 73/31.05; 73/23.2; 204/424
(58) Field of Search .................... 73/23.2, 31.05; 204/424

(56) References Cited

U.S. PATENT DOCUMENTS

| | | | |
|---|---|---|---|
| 4,656,863 A | * | 4/1987 | Takami et al. ............. 73/31.05 |
| 5,817,920 A | | 10/1998 | Kuisell et al. |
| 5,886,248 A | | 3/1999 | Paulus et al. |
| 6,063,249 A | | 5/2000 | Duce et al. |

FOREIGN PATENT DOCUMENTS

| | | |
|---|---|---|
| EP | 0932039 A2 | 7/1999 |
| EP | 0939314 A2 | 9/1999 |
| JP | 11-513113 | 11/1999 |

OTHER PUBLICATIONS

"Metals Handbook", Handbook Committee, Jun. 1985, American Society for Metals, Ninth edition, vol. 8 (Mechanical Testing), p. 13.*

* cited by examiner

*Primary Examiner*—Michael Cygan
(74) *Attorney, Agent, or Firm*—Nixon & Vanderhye PC (57) ABSTRACT

A gas sensing element is placed in an element insertion hole of an insulator. The element insertion hole consists of a larger-diameter portion and a smaller-diameter portion. A clearance between an inner surface of the larger-diameter portion and an outer surface of the gas sensing element is filled with a sealing material. A clearance between an inner surface of the smaller-diameter portion and the outer surface of the gas sensing element is filled with a cushion filler having the capability of withstanding a loading force ranging from 5N to 1,000N.

16 Claims, 9 Drawing Sheets

GAS SENSOR

BACKGROUND OF THE INVENTION

The present invention relates to a gas sensor utilized for an air-fuel ratio control of an internal combustion engine.

A gas sensor is installed in an exhaust system of an automotive engine for air-fuel ratio control or the like.

A conventional gas sensor comprises a cylindrical insulator having an element insertion hole, a gas sensing element airtightly fixed in the element insertion hole, and a cylindrical housing having an inside space for placing the insulator. An air side cover is attached to a proximal end of the housing so as to confine an aerial atmosphere therein. And, a measured gas side cover is attached to a distal end of the housing so as to confine a measured gas atmosphere therein.

Figure 13:
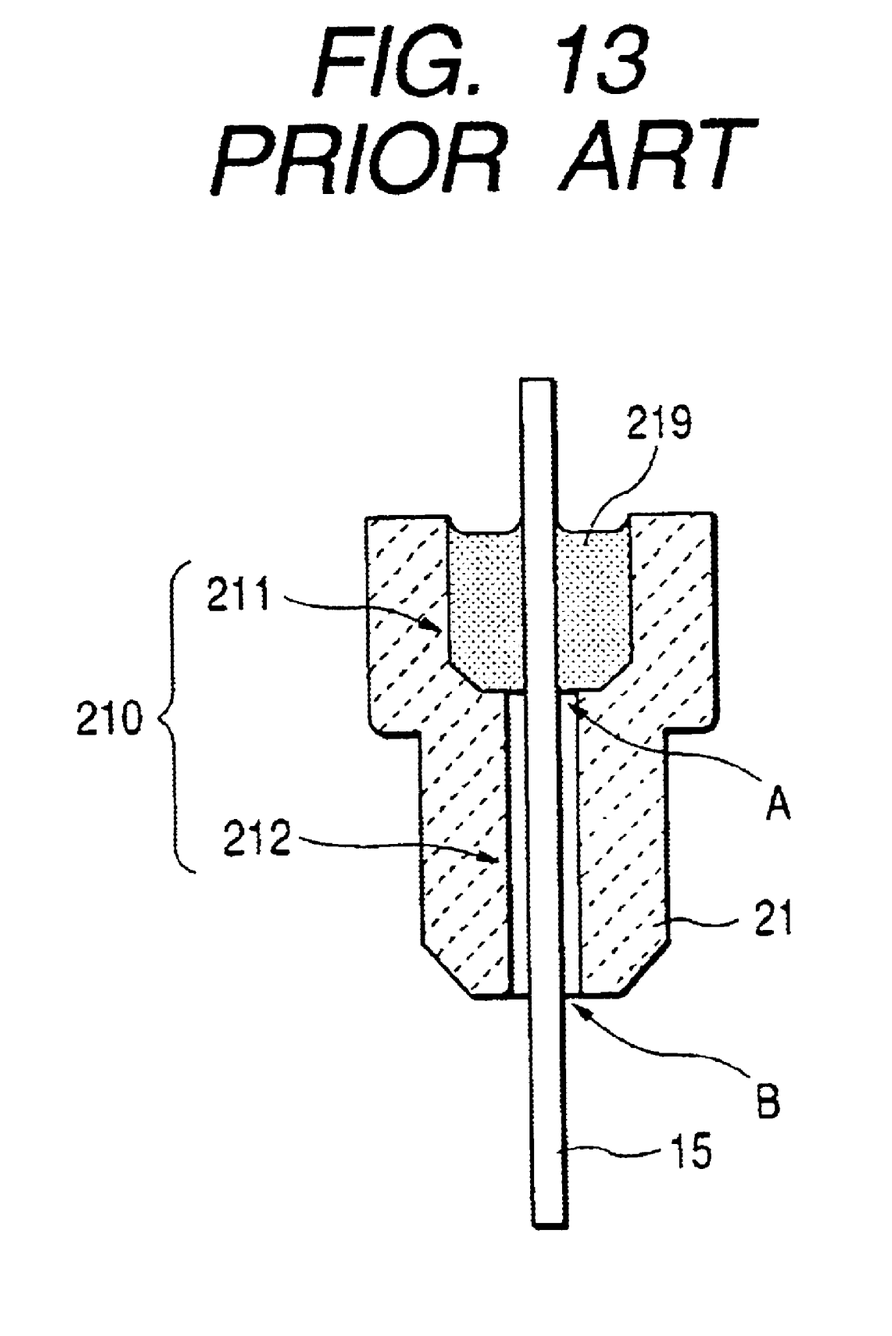
FIG. 13 is a vertical cross-sectional diagram showing a conventional gas sensor comprising a gas sensing element inserted in an insulator.

As shown in FIG. 13, to facilitate insertion of the gas sensing element 15, the element insertion hole 210 consists of a larger-diameter portion 211 formed at the proximal end thereof and a smaller-diameter portion 212 formed at the distal end thereof. The larger-diameter portion 211 has an inner diameter larger than that of the smaller-diameter portion 212.

A sealing material 219 is interposed between an outer surface of the gas sensing element 15 and an inner surface of the larger-diameter portion 211 of the element insertion hole 210 to firmly seal the clearance between them.

The clearance between the gas sensing element 15 and the element insertion hole 210 corresponds to a boundary between the aerial atmosphere and the measured gas atmosphere. It is therefore necessary to airtightly seal the clearance between the gas sensing element 15 and the element insertion hole 210 to surely separate the aerial atmosphere and the measured gas atmosphere.

However, according to the above-described conventional sensor, the smaller-diameter portion 212 is spaced from the gas sensing element 15 via a significant clearance. The gas sensing element 15 is supported at its proximal end with the sealing material 219 in a cantilever fashion.

Accordingly, when a large shock or vibration is applied from the outside, the gas sensing element will swing like a pendulum and may collide with the inner surface of the smaller-diameter portion 212. Thus, the has sensing element is often subjected to a concentrated stress and broken or damaged.

FIG. 13 shows a portion "A" where the concentrated stress acts to the gas sensing element 15 and a portion "B" where an edged portion of the insulator 21 faces to the gas sensing element 15. Accordingly, the gas sensing element 15 is often broken at these specific portions.

U.S. Pat. No. 5,886,248 discloses a gas sensor comprising a sealing material provided in a clearance between the gas sensing element and the insulator so as to extend from the proximal end to a distal end thereof.

However, as this sealing material is a hard substance, it has difficulty in preventing the gas sensing element from cracking or breaking when a large shock is applied from the outside, although such a rigid sealing material may be effective against swinging of the gas sensing element.

SUMMARY OF THE INVENTION

To solve the above-described problems, an object of the present invention is to provide a gas sensor which prevents the gas sensing element from cracking and breaking.

To accomplish the above and other related objects, the present invention provides a first gas sensor comprising a cylindrical insulator having an element insertion hole extending from a proximal end to a distal end thereof, a gas sensing element airtightly fixed in the element insertion hole of the insulator, and a cylindrical housing having an inside space for placing the insulator, with an air side cover attached to a proximal end of the housing so as to confine an aerial atmosphere therein and a measured gas side cover attached to a distal end of the housing so as to confine a measured gas atmosphere therein. According to the first gas sensor, a sealing material is provided at one side of the element insertion hole for sealing a clearance between an inner surface of the element insertion hole and an outer surface of the gas sensing element. And, a cushion filler, having the capability of withstanding a loading force ranging from 5N to 1,000N, is provided at the other side of the element insertion hole for sealing a clearance between the inner surface of the element insertion hole and the outer surface of the gas sensing element.

The present invention is characterized in that one end of the gas sensing element is fixed with the sealing material and the other end of the gas sensing element is supported by a soft cushion filler having the strength within the above-described range.

Effects of the present invention will be explained hereinafter.

The cushion filler of the present invention is so soft that it can sufficiently absorb shocks applied from the outside.

Thus, it becomes possible to prevent the gas sensing element from being directly subjected to shocks transmitted from the outside of the gas sensor.

Furthermore, as the gas sensing element of the present invention is held at both of its proximal end and its distal end, the gas sensing element does not swing like a pendulum when it receives shocks or vibrations.

Accordingly, the present invention prevents a concentrated stress from acting on a portion serving as a swing center of the gas sensing element (i.e., a portion immediately below the portion firmly fixed with the sealing material) and also prevents the gas sensing element from colliding with the inner surface of the insulator. Therefore, the present invention effectively prevents the gas sensing element from cracking or breaking.

If the loading force of the cushion filler is less than 5N, insertion of the cushion filler will be difficult. If the loading force of the cushion filler is larger than 1,000N, a large concentrated stress responsive to an external shock will act on the gas sensing element via the cushion filler. This external shock may crack or break the gas sensing element.

In view of facilitating insertion of the cushion filler, it is preferable that the loading force of the cushion filler is equal to or larger than 20N.

Furthermore, the cushion filler can effectively absorb the shock applied from the outside when the loading force of the cushion filler is equal to or less then 400N.

Furthermore, according to the present invention, the clearance between the insulator and the proximal end of the gas sensing element is filled with a dense and hard substance, such as the sealing material. As described previously, the clearance between the gas sensing element and the element insertion hole corresponds to the boundary between the aerial atmosphere and the measured gas atmosphere. Thus, the sealing material interposed between the gas sensing element and the element insertion hole surely separates the aerial atmosphere and the measured gas atmosphere.

As described above, the present invention can provide a gas sensor capable of preventing cracks and breakage of the gas sensing element.

Furthermore, as described later in a preferred embodiment of the present invention, the present invention is applicable to a gas sensor incorporating a multilayered flat plate sensing element and is also applicable to a gas sensor incorporating a cup-shaped solid electrolytic sensing element.

Furthermore, the gas sensor of the present invention is applicable to an air-fuel ratio sensor and to an oxygen sensor installed in an exhaust system of an internal combustion engine, and is also applicable to various sensors, such as a NOx sensor, a CO sensor, and an HC sensor.

The sealing material of the present invention is, for example, glass, talc, steatite, zirconia, and alumina.

The cushion filler of the present invention is, for example, a heat-resistance substance, such as zirconia or ceramic, which has a thermal expansion coefficient similar to that of the insulator or the gas sensing element.

Especially, when the cushion filler of the present invention is used in an exhaust system described in a preferred embodiment, it is subjected to high temperature exhaust gas. Thus, it is preferable that the above-described conditions are satisfied to assure the durability in a wide temperature range from the room temperature to such high temperatures.

Talc, mullite, zirconia, steatite can be also used as the cushion filler of the present invention.

When a gas sensor is solely used in a portion where the heat-resistance is not so important, various resin materials, such as PTFE (i.e., polytetrafluorethylene), fluororubber, NBR (i.e., nitrile-butadien rubber), can be also used as the cushion filler of the present invention.

Furthermore, to fill the element insertion hole with the cushion filler, a powdered material can be hardly pushed into the element insertion hole so as to serve as the cushion filler of the present invention.

Furthermore, it is possible to prepare a slurry by kneading a powered material with a binder, and injecting the slurry into the element insertion hole, and then sintering the injected slurry.

Furthermore, a dry-hardening type adhesive can be used as the cushion filler of the present invention.

Furthermore, the effect of the present invention can be obtained even if some cavities or hollow portions exist in the cushion filler.

Next, according to the present invention, it is preferable that a filling rate of the cushion filler provided between the inner surface of the element insertion hole and the outer surface of the gas sensing element is in the range from 10% to 80%.

This makes it possible to improve the strength of the cushion filler against the shock applied from the outside.

If the filling rate of the cushion filler is less than 10%, the amount of the cushion filler will be insufficient for surely holding the gas sensing element.

If the filling rate of the cushion filler is larger than 80%, the effect of absorbing the shock will be weakened and the gas sensing element may cause crack or breakage.

Next, according to the present invention, it is preferable that an injection port is provided near an open edge of the element insertion hole at the distal end of the insulator for facilitating a filling operation of the sealing material or the cushion filler.

With this arrangement, the sealing material or the cushion filler can be easily injected into the element insertion hole.

Figure 4A:
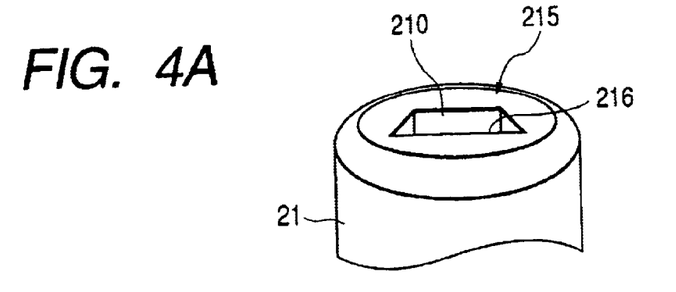
FIG. 4A is a perspective diagram showing an open edge of an insulator in accordance with the first embodiment of the present invention.
Figure 4B:
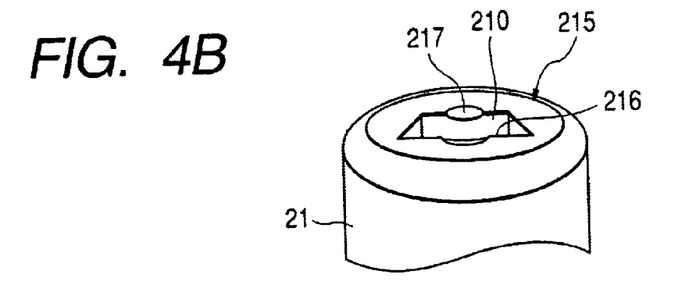
FIG. 4B is a perspective diagram showing an open edge of the insulator with an injection port in accordance with the first embodiment of the present invention.

The injection port is, for example, a recess formed along the open edge (refer to FIG. 4B).

Next, according to the present invention, it is preferable that the element insertion hole comprises a larger-diameter portion at one end and a smaller-diameter portion at the opposite end, and an inner diameter of the larger-diameter portion is larger than that of the smaller-diameter portion.

With this arrangement, the strength against the external shock can be improved.

Next, according to the present invention, it is preferable that the sealing material and/or the cushion filler is placed so as to fix at least two opposed surfaces of the inner surface of the element insertion hole and the outer surface of the gas sensing element.

With this arrangement, the strength against the external shock can be enhanced.

The present invention further provides a second gas sensor comprising a cylindrical insulator having an element insertion hole extending from a proximal end to a distal end thereof, a gas sensing element airtightly fixed in the element insertion hole of the insulator, and a cylindrical housing having an inside space for placing the insulator, with an air side cover attached to a proximal end of the housing so as to confine an aerial atmosphere therein and a measured gas side cover attached to a distal end of the housing so as to confine a measured gas atmosphere therein. According to the second gas sensor, a sealing material is provided at one side of the element insertion hole for sealing a clearance between an inner surface of the element insertion hole and an outer surface of the gas sensing element. A cushion filler, having the capability of withstanding a loading force ranging from 5N to 1,000N, is provided at the other side of the element insertion hole for sealing a clearance between the inner surface of the element insertion hole and the outer surface of the gas sensing element. The insulator constitutes a main body and a separate body attached via a spacer to a distal end of the main body, so that the element insertion hole extends across both of the main body and the separate body. And, the cushion filler is provided only in the element insertion hole of the separate body.

The cushion filler of the present invention is so soft that it can sufficiently absorb shocks applied from the outside.

Thus, it becomes possible to prevent the gas sensing element from being directly subjected to shocks transmitted from the outside of the gas sensor.

Furthermore, as the gas sensing element of the present invention is held at both of its proximal end and its distal end, the gas sensing element does not swing like a pendulum when it receives shocks or vibrations.

Accordingly, the present invention prevents a concentrated stress from acting on a portion serving as a swing center of the gas sensing element (i.e., a portion immediately below the portion firmly fixed with the sealing material) and also prevents the gas sensing element from colliding with the inner surface of the insulator. Therefore, the present invention effectively prevents the gas sensing element from cracking or breaking.

If the loading force of the cushion filler is less than 5N, insertion of the cushion filler will be difficult. If the loading force of the cushion filler is larger than 1,000N, a large concentrated stress responsive to an external shock will act on the gas sensing element via the cushion filler. This external shock may crack or break the gas sensing element.

Furthermore, according to the present invention, the clearance between the insulator and the proximal end of the gas sensing element is filled with a dense and hard substance, such as the sealing material. As described previously, the clearance between the gas sensing element and the element insertion hole corresponds to the boundary between the aerial atmosphere and the measured gas atmosphere. Thus, the sealing material interposed between the gas sensing element and the element insertion hole surely separates the aerial atmosphere and the measured gas atmosphere.

Furthermore, as the insulator constitutes the main body and the separate body attached via the spacer to the distal end of the main body, the external shock can be effectively absorbed by the spacer. This enhances the strength against the external shock.

Furthermore, as the cushion material is solely provided at the separate body, the filling operation of the cushion filler can be easily performed.

As described above, the present invention can provide a gas sensor capable of preventing cracks and breakage of the gas sensing element.

BRIEF DESCRIPTION OF THE DRAWINGS

The above and other objects, features and advantages of the present invention will become more apparent from the following detailed description which is to be read in conjunction with the accompanying drawings, in which.

DESCRIPTION OF THE PREFERRED EMBODIMENTS

Preferred embodiments of the present invention will be explained hereinafter with reference to attached drawings. Identical parts are denoted by the same reference numerals throughout the drawings. In the following description, a front side of a gas sensor to be exposed to a measured gas is referred to as a distal end side and the opposite side is referred to as a proximal end side.

First Embodiment

Hereinafter, a gas sensor according to a first embodiment of the present invention will be explained with reference to FIGS. 1 to 7.

Figure 1:
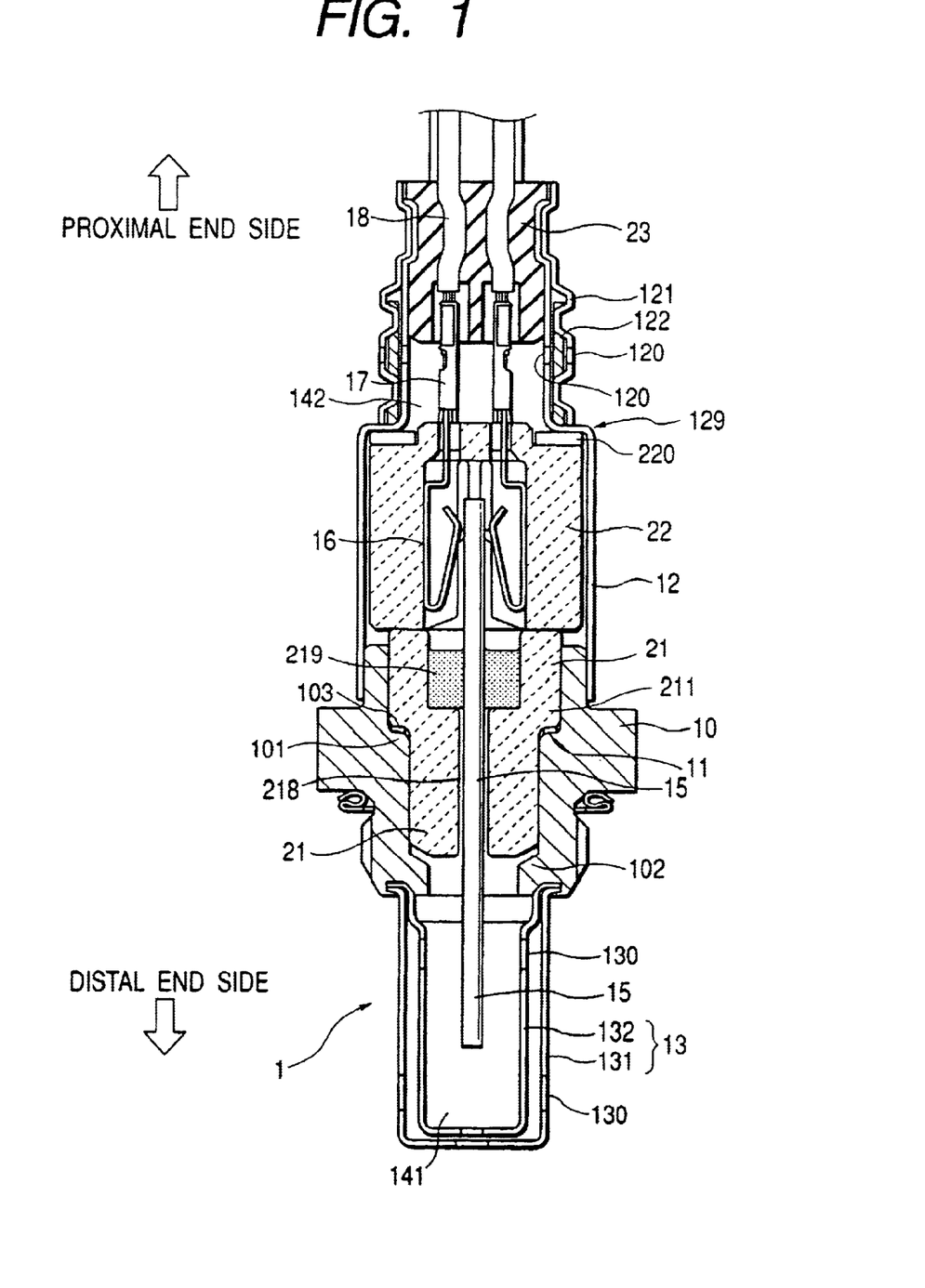
FIG. 1 is a vertical cross-sectional diagram showing a gas senor in accordance with a first embodiment of the present invention.
Figure 2:
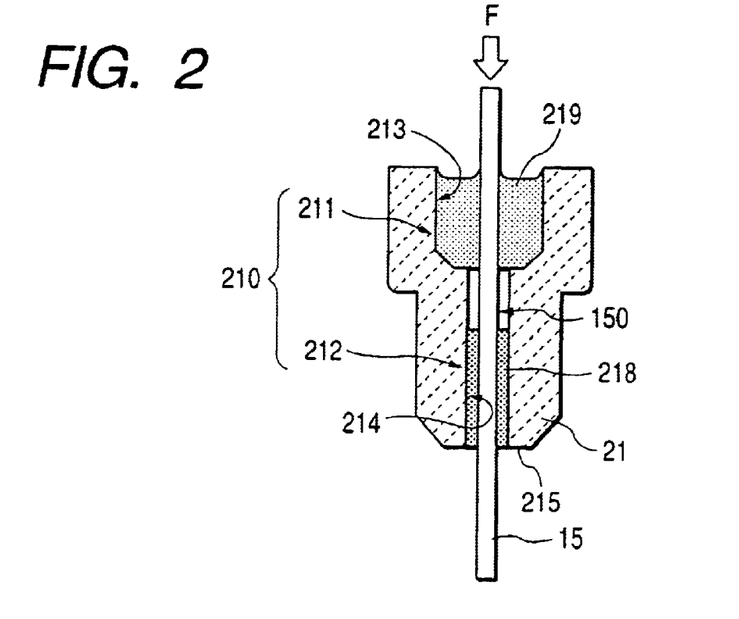
FIG. 2 is a vertical cross-sectional diagram showing a cushion filler placed in an element insertion hole in accordance with the first embodiment of the present invention.

As shown in FIGS. 1 and 2, a gas sensor 1 of this embodiment comprises a insulator 21 having an element insertion hole 210 extending from a proximal end to a distal end thereof, a gas sensing element 15 airtightly fixed in the element insertion hole 210 of the insulator 21, and a cylindrical housing 10 having an inside space for placing the insulator 21, with an air side cover 12 attached to a proximal end of the housing 10 so as to confine an aerial atmosphere 142 therein and a measured gas side cover 13 attached to a distal end of the housing 10 so as to confine a measured gas atmosphere 141 therein.

As shown in FIG. 2, the element insertion hole 210 consists of a larger-diameter portion 211 formed at the proximal end thereof and a smaller-diameter portion 212 formed at the distal end thereof. The larger-diameter portion 211 has an inner diameter larger than that of the smaller-diameter portion 212. A sealing material 219 is provided at the proximal end side of the element insertion hole 210 for sealing a clearance between an inner surface 213 of the element insertion hole 210 (i.e., a larger-diameter portion 211) and an outer surface 150 of the gas sensing element 15. And, a cushion filler 218, having the capability of withstanding a loading force ranging from 5N to 1,000N, is provided at the distal end side of the element insertion hole 210 for sealing a clearance between an inner surface 214 of the element insertion hole 210 (i.e., smaller-diameter portion 212) and the outer surface 150 of the gas sensing element 15.

Hereinafter, this embodiment will be explained in more detail.

The gas sensor 1 of this embodiment is installed in an exhaust system of an automotive internal combustion engine and is used for an air-fuel ratio control of the internal combustion engine.

As shown in FIG. 1, in the gas sensor 1, the measured gas side cover 13 attached at the distal end of the housing 10 consists of an outer cover 131 and an inner cover 132 cooperatively constituting a double-layer construction. Both of the outer cover 131 and the inner cover 132 are provided with holes 130 through which the measured gas is introduced into the measured gas side cover 13 so as to form the measured gas atmosphere 141.

The air side cover 12 is provided at the proximal end of the housing 10. An outer cover 121 is overlapped with an outer surface of the air side cover 12 at a proximal end thereof via a water-repellent filter 122. The overlapped portions of the air side cover 12 and the outer cover 121 are provided with holes 120 for introducing air inside the air side cover 12 via the water-repellent filter 122.

The air side cover 12 has a smaller-diameter portion at its proximal end and a larger-diameter portion at its distal end which are integrally and continuously formed via a stepped portion 129.

The air introduced in the air side cover 12 through the air-introducing holes 120 forms the aerial atmosphere 142.

As shown in FIGS. 1 and 2, the housing 10 is configured into a cylindrical shape and has two protrusions 101 and 102 protruding radially inward from an inner surface thereof.

The protrusion 101, positioned at the proximal end side, has a receiving surface 103 which supports a tapered portion provided at an outer surface of the insulator 21.

The tapered portion is supported on the receiving surface 103 via an annular metallic packing 11. The inside space of the gas sensor 1 is airtightly separated into the aerial atmosphere 142 and the measured gas atmosphere 141 at the portion where the metallic packing 11 is disposed.

An air side insulator 22 is disposed at a proximal end of the insulator 21. An annular disc spring 220 is disposed between the air side insulator 22 and the stepped portion 129 of the air side cover 12.

A total of four leads 16 are disposed in an inside space of the air side insulator 22 so as to be electrically conductive with the gas sensing element 15.

The gas sensing element 15, used for detecting an oxygen concentration, is a multilayer type equipped with a built-in heater. Although not shown in the drawing, the gas sensing element 15 has two sensor electrodes for taking out a sensor output signal, two power electrodes for supplying electric power to the heater, and a total of four electrode terminals taken out of the sensor body.

The four leads 16 are disposed so as to be brought into contact with these four electrode terminals respectively.

A proximal end of each lead 16 is connected to a lead 18 via a connector 17 at an outside of the air side insulator 22. The lead 18 extends out of the gas sensor 1 through an elastic insulating member 23 disposed at a proximal end side of the air side cover 12.

As shown in FIG. 2, the gas sensing element 15 is inserted into the element insertion hole 210 of the insulator 21. A proximal end side of the gas sensing element 15 is firmly fixed to the larger-diameter portion 211 of the insulator 21 by the sealing material 219 made of crystallized glass. A distal end side of the gas sensing element 15 is softly held via the cushion filler 218 by the smaller-diameter portion 212.

The cushion filler 218 is made of alumina having the capability of withstanding a loading force ranging from 50N to 100N (refer to a later-described method for filling the cushion filer).

As shown in FIG. 2, the cushion filler 218 extends from the distal end of the insulator 21 to an approximately center of the smaller-diameter portion 212 so as to airtightly seal the clearance between the gas sensing element 15 and the smaller-diameter portion 212 of the element insertion hole 210.

Figure 3:
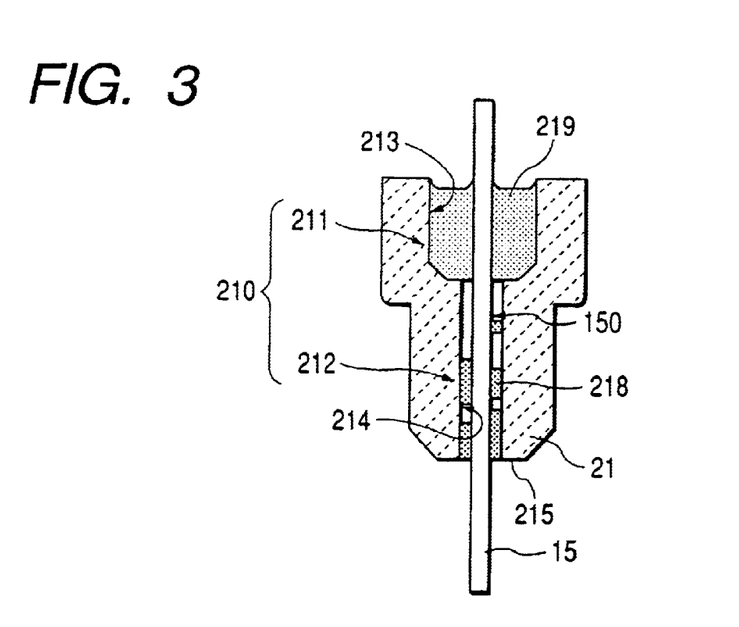
FIG. 3 is a vertical cross-sectional diagram showing a cushion filler placed discretely in an element insertion hole in accordance with the first embodiment of the present invention.

Furthermore, it is allowable that cavities may exist discretely in the cushion filler 218 as shown in FIG. 3.

As shown in FIG. 4A, an open edge 216 of the element insertion hole 210 is formed on a distal end surface 215 of the insulator 21. The cushion filler 218 is inserted into the element insertion hole 210 from the open edge 216 to fill the insertion hole 210.

As shown in FIG. 4B, it is preferable to provide an injection port 217 near the open edge 216 to facilitate a filling operation of the cushion filler 218.

The injection port 217 is a semicircular recess merged into the element insertion hole 210 via the open edge 216.

Next, the method for filling the cushion filler 218 into the element insertion hole 210 will be explained.

First, the gas sensing element 15 is inserted into the insulator 21. Then, the sealing material 219 is filled in the large-diameter portion 211 of the element insertion hole 210 to securely fix the proximal end of the gas sensing element 15.

Then, a slurry of alumina is injected into the element insertion hole 210 from the open edge 216. This slurry is formed by kneading alumina powder with alumina sol serving as a binder.

Subsequently, the slurry is heated together with the insulator 21 and the gas sensing element 15 to volatilize the binder, thereby firmly binding alumina grains to form the cushion filler 218.

To check the effect of providing the cushion filler 218 in the gas sensor according to this embodiment, an evaluation test was conducted.

As the cushion filler 218 for the gas sensor according to the present invention, a gas sensor sample 1 relating to SC—AL and a gas sensor sample 2 relating to SC-574 were prepared. Furthermore, as a comparison, a comparative gas sensor sample C1 equipped with no cushion filler was additionally prepared (refer to FIG. 13).

The gas sensor sample 1 relating to SC—AL was formed by filling γ-alumina powder having a particle diameter of 4 μm and porosity of 45% into the element insertion hole 210 to form the cushion filler 218 according to the above-described method.

The gas sensor sample 2 relating to SC-574 was formed by filling γ-alumina powder having a particle diameter of 15 μm and porosity of 60% into the element insertion hole 210 to form the cushion filler 218 according to the above-described method.

Numerous gas sensor samples 1 and 2 and the comparative sample C1 were prepared to conduct a drop test.

The performed drop test includes a step of dropping each sample from a predetermined height, a step of activating a built-in heater of a gas sensing element of each tested sample, and a step of checking whether or not the heater is operating normally.

Figure 5:
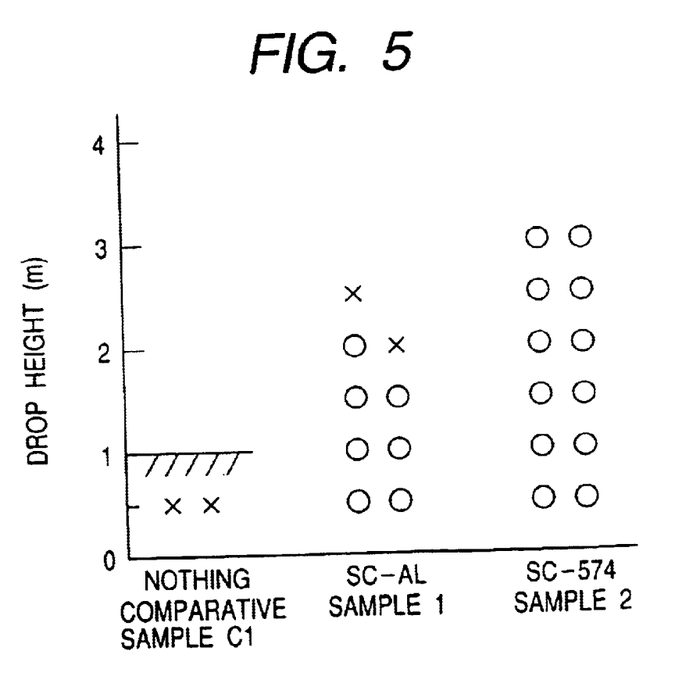
FIG. 5 is a graph showing a relationship between occurrence of abnormality and the drop height of each tested sample in accordance with the first embodiment of the present invention and a comparative sample.

FIG. 5 shows the result of the drop test.

The result of FIG. 5 reveals that the comparative sample C1 has caused disorder even when it was dropped from a relatively lower height of 50 cm. It is believed that the gas sensing element was broken or damaged due to the shock resulting from the drop test and, accordingly, the heater wiring was also broken.

On the contrary, the sample 1 incorporating the cushion filler 218, according to this embodiment, caused no disorder unless the drop height was greater than 1.5 m.

Furthermore, the sample 2 of this embodiment has caused no disorder even if it was dropped from a height of 3 m.

From the foregoing, it is confirmed that the cushion filer 218 according to this embodiment effectively prevents the gas sensing element from cracking or breaking when the gas sensor is dropped. Furthermore, it is confirmed that the cushion filler 218 having a larger particle diameter and high porosity shows better properties.

Furthermore, the gas sensor samples 1 and 2 were subjected to an additional test to check whether the gas sensing element 15 moves or not when a load is applied from the proximal end of the gas sensing element in a condition where the gas sensing element 15 is inserted in the insulator 21, as shown in FIG. 2. The load applied from the proximal end of the gas sensing element 15 is shown by an arrow F in FIG. 2.

For comparison with the samples 1 and 2, another comparative sample C2 is prepared as characterized in that the cushion filler 218 is replaced by the same material as the sealing material 219.

According to the test result, the gas sensing element of sample 1 has moved when the applied load exceeded 200N and the gas sensing element of sample 2 has moved when the applied load exceeded 400N. On the contrary, the gas sensing element of the comparative sample C2 did not move until the applied load reaches 1,500N.

Meanwhile, the comparative sample C2 was subjected to the drop test according to which trouble was caused in the power supply to the heater. As a result, it is confirmed that using rigid or hard sealing material is not effective to prevent the gas sensing element from being damaged.

The cushion filler 218 of this embodiment is so soft that it can sufficiently absorb the shock applied from the outside. Thus, it becomes possible to prevent the shock from being directly transmitted to the gas sensing element 15.

Furthermore, as the gas sensing element 15 of this embodiment is held at both of its proximal end and its distal end, the gas sensing element 15 does not swing like a pendulum when it receives shocks or vibrations.

Accordingly, this embodiment prevents a concentrated stress from acting on a portion serving as a swing center of the gas sensing element (i.e., a portion immediately below the portion firmly fixed with the sealing material) and also prevents the gas sensing element from colliding with the inner surface of the insulator. Therefore, this embodiment effectively prevents the sensing element from cracking or breaking.

Furthermore, according to this embodiment, the clearance between the insulator 21 and the proximal end of the gas sensing element 15 is filled with a dense and hard substance, such as the sealing material 219.

The cushion filler 218 of this embodiment is made of alumina and therefore has so large porosity that it cannot serve as an airtight seal.

As apparent from FIG. 1, as well as the clearance between the inner surface of the housing 10 and the outer surface of the insulator 21, the clearance between the gas sensing element 15 and the element insertion hole 210 corresponds to a boundary between the aerial atmosphere and the measured gas atmosphere. Thus, the sealing material 219 interposed between the gas sensing element 15 and the element insertion hole 210 surely separates the aerial atmosphere and the measured gas atmosphere.

As apparent from the foregoing description, this embodiment provides a gas sensor causing no cracks and breakage of the gas sensing element.

Figure 6:
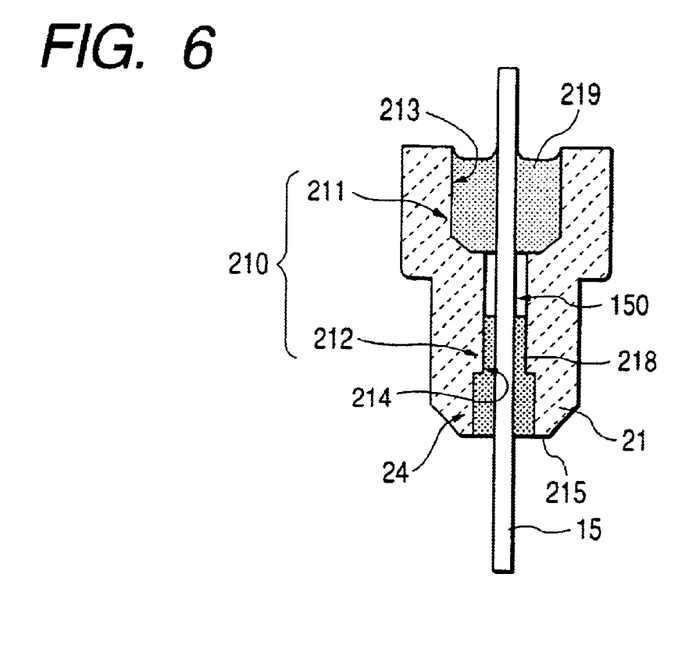
FIG. 6 is a vertical cross-sectional diagram showing an element insertion hole whose inner diameter is changed stepwise at an intermediate portion thereof in accordance with the first embodiment of the present invention.

According to the gas sensor 1 of this embodiment, the smaller-diameter portion 212 of the element insertion hole 210 extends straight in the axial direction with a constant diameter. As shown in FIG. 6, it is also preferable to configure the smaller- diameter portion 212 into a stepped bore 24 having an enlarged diameter at the distal end thereof.

This arrangement brings an effect of facilitating the insertion of the cushion filler 218 in addition to the above-described effects.

Figure 7:
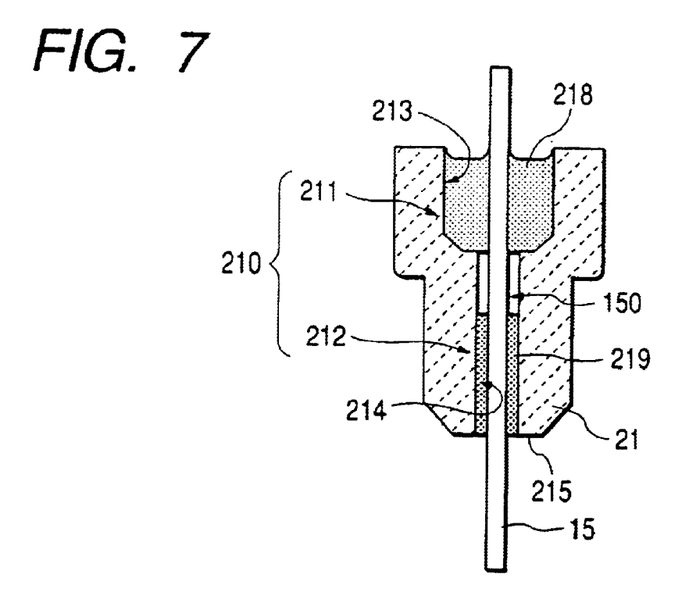
FIG. 7 is a vertical cross-sectional diagram showing a cushion filler provided at a proximal end of the element insertion hole and a sealing material provided at a distal end of the element insertion hole in accordance with the first embodiment of the present invention.

Furthermore, as shown in FIG. 7, the gas sensor 1 of this embodiment can be modified in such a manner that the smaller-diameter portion 212 of the element insertion hole is filled with the sealing material 219 and the larger-diameter portion 211 is filled with the cushion filler 218.

Numerous gas sensors relating to samples 2 of the first embodiment were prepared, although the filling percentage of the cushion filler 218 relative to the element insertion hole 210 was differentiated in each gas sensor.

Each gas sensor was subjected to the drop test.

Figure 8:
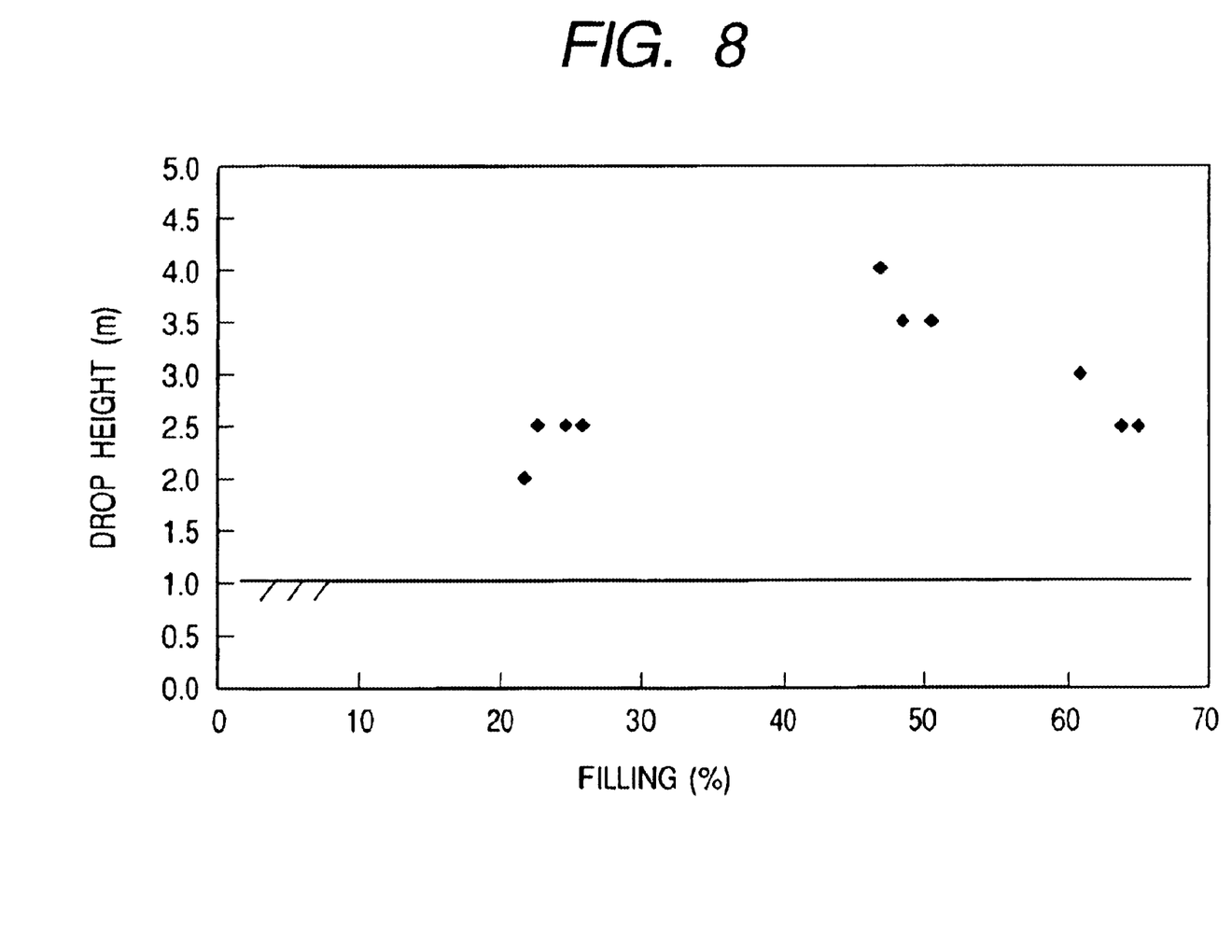
FIG. 8 is a graph showing a relationship between a filling rate of the cushion filler and the drop height in accordance with the first embodiment of the present invention.

FIG. 8 shows the highest position achieved by each sample in the drop test as a limit causing no damage in the tested sample.

As shown in FIG. 8, the sample whose filling percentage of the cushion filler 218 is 50% showed the best property.

Second Embodiment

Figure 9:
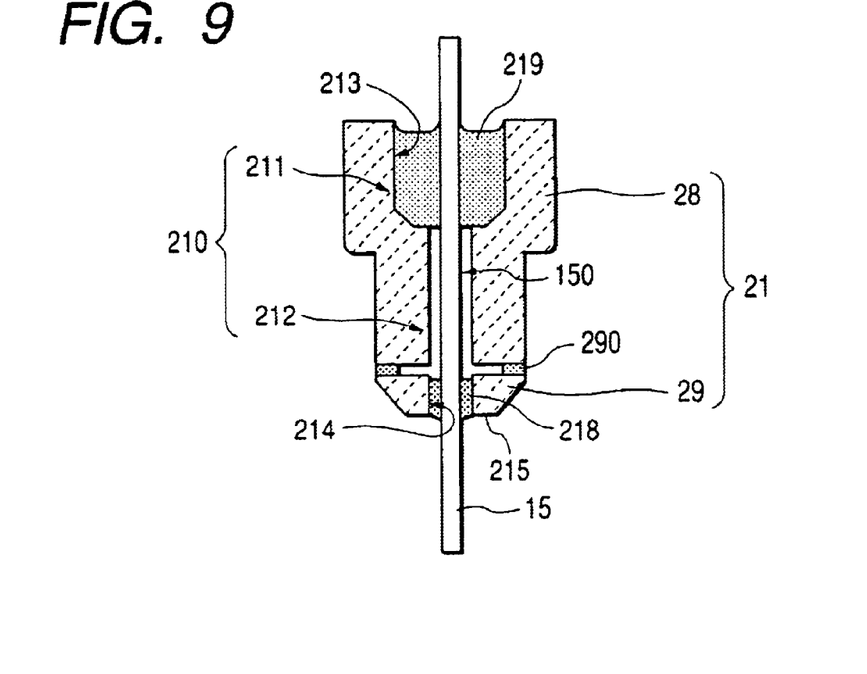
FIG. 9 is a vertical cross-sectional diagram showing an insulator consisting of a main body and a separate body in accordance with a second embodiment of the present invention.

As shown in FIG. 9, a second embodiment is characterized in that the insulator 21 consists of a main body 28 and a separate body 29. The element insertion hole 210 extends across both of the main body 28 and the separate body 29. The separate body 29 is attached to a distal end of the main body 28 via a spacer 290. The smaller-diameter portion 212 of the element insertion hole extends from the main body 28 to the separate body 29.

The cushion filler 218 is provided only in the smaller-diameter portion 212 of the separate body 29.

The rest of the arrangement is similar to that of the first embodiment.

The gas sensor in accordance with the second embodiment has the insulator 21 comprising the separate body 29 attached to the main body 28 via the spacer 290. Thus, the shock applied from the outside can be absorbed by the spacer 290. Thus, the strength against the external shock can be further increased.

Furthermore, as the cushion filler 218 is provided only in the separate body 29, the filling operation of the cushion filler can be easily performed. Details of the remaining arrangement is similar to those disclosed in the first embodiment.

Third Embodiment

Figure 10:
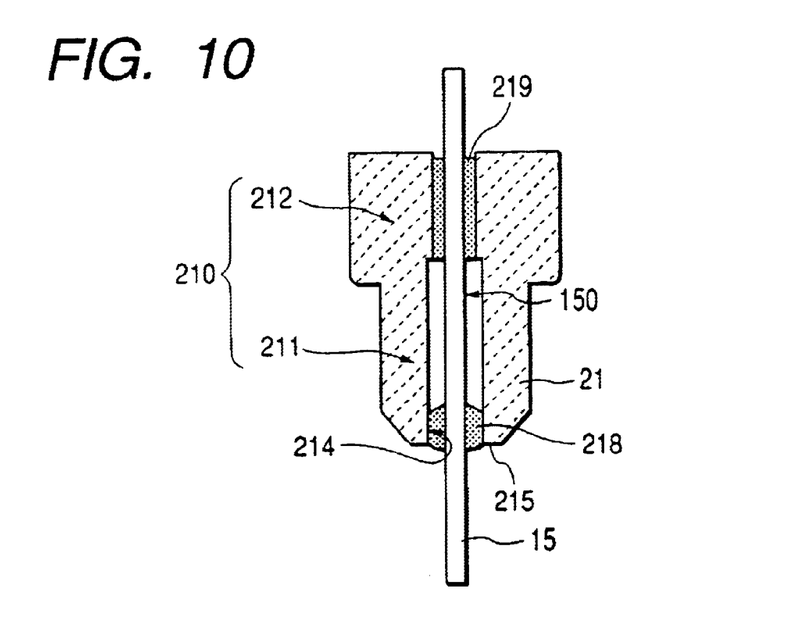
FIG. 10 is a vertical cross-sectional diagram showing an element insertion hole having a smaller-diameter portion at the proximal end thereof and a larger-diameter portion at the distal end thereof in accordance with a third embodiment of the present invention.

As shown in FIG. 10, a third embodiment is characterized in that the element insertion hole 210 consists of a larger-diameter portion 211 formed at the distal end thereof and a smaller-diameter portion 212 formed at the distal end thereof. The larger-diameter portion 211 has an inner diameter larger than that of the smaller-diameter portion 212. The clearance between the inner surface of the larger-diameter portion 211 and the gas sensing element 15 is filled with the cushion filler 218. The clearance between the inner surface of the smaller-diameter portion 212 and the gas sensing element 15 is filled with the sealing material 219.

The rest of arrangement is similar to that of the first embodiment.

This embodiment provides a gas sensor which is strong against external shock. Details of the remaining arrangement is similar to those disclosed in the first embodiment.

Fourth Embodiment

Figure 11:
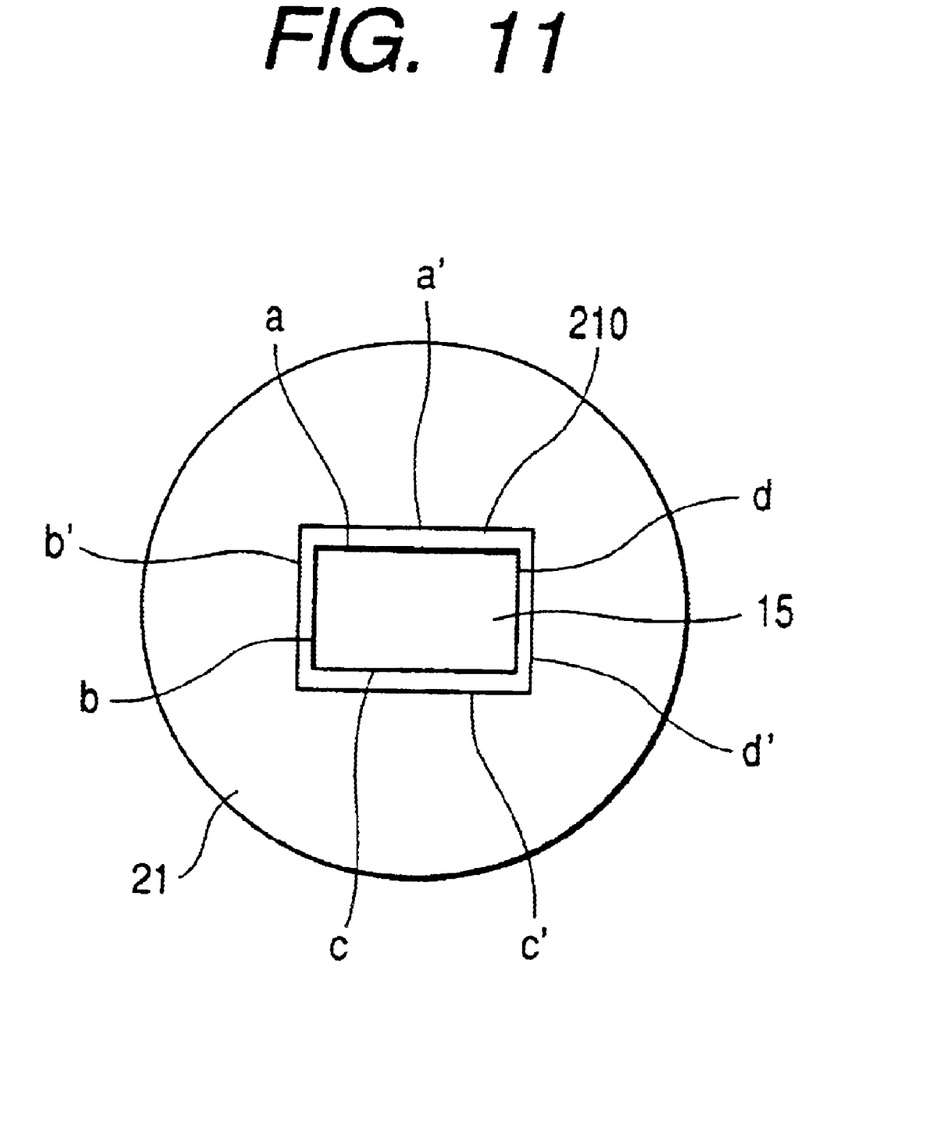
FIG. 11 is a transverse cross-sectional diagram showing an insulator and a gas sensing element in accordance with a fourth embodiment of the present invention.

FIG. 11 shows the gas sensing element 15 fixed to a surface of the element insertion hole 210.

As shown in FIG. 11, the gas sensing element 15 has a rectangular cross section. The element insertion hole 210 has a rectangular cross section similar to that of the gas sensing element 15.

The clearance between the element insertion hole 210 and the gas sensing element 15 is filled with the cushion filler or the sealing material (not shown) so that two opposed surfaces can be fixed to each other.

In this case, each combination of surfaces a–a', b–b', c–c' and d–d' are two opposed surfaces.

Especially, it is preferable to firmly fix the longer sides a–a' and c–c'.

The rest of the arrangement is similar to that of the first embodiment.

This embodiment provides a gas sensor which is strong against the external shock. Details of the remaining arrangement is similar to those disclosed in the first embodiment.

Fifth Embodiment

Figure 12A:
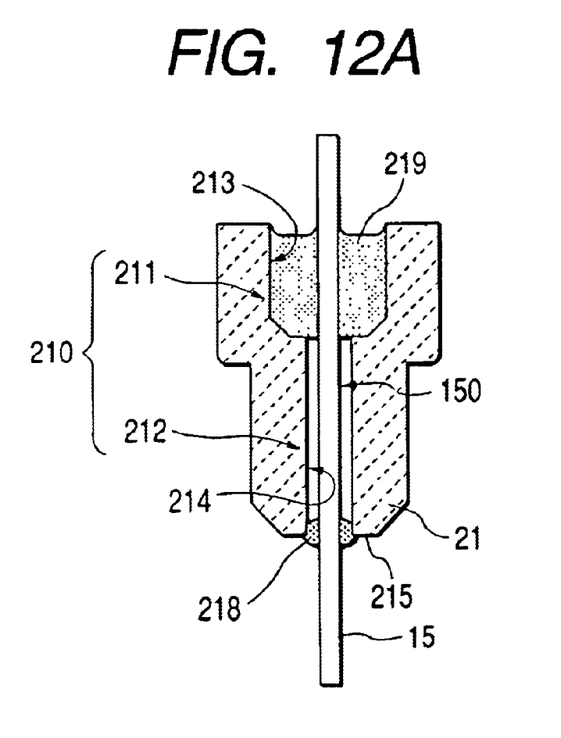
FIG. 12A is a vertical cross-sectional diagram showing a cushion filler partly protruding from the distal end of the element insertion hole in accordance with a fifth embodiment of the present invention.
Figure 12B:
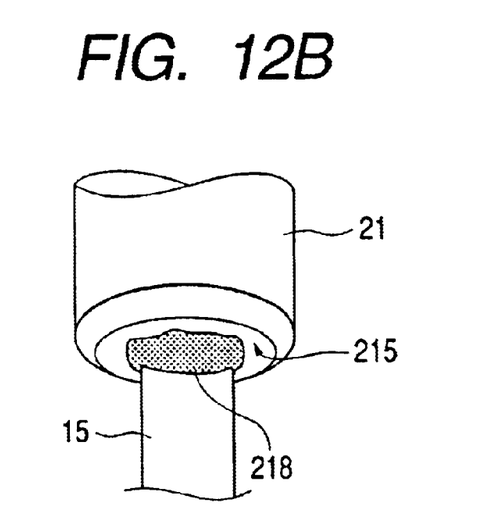
FIG. 12B is an enlarged diagram showing details of the cushion filler shown in FIG. 12A.

As shown in FIG. 12A, a fifth embodiment comprises the gas sensing element 15 fixed to the element insertion hole 210 via the sealing material 219 filled in the larger-diameter portion 211 and the cushion filler 218 filled in the smaller-diameter portion 212. And, as shown in FIG. 12B, the cushion filler 218 partly protrudes out of the element insertion hole 210 beyond the distal end surface 215.

The rest of the arrangement is similar to that of the first embodiment.

This embodiment provides a gas sensor which is strong against the external shock. Details of the remaining arrangement is similar to those disclosed in the first embodiment.

This invention may be embodied in several forms without departing from the spirit of essential characteristics thereof. The present embodiments as described are therefore intended to be only illustrative and not restrictive, since the scope of the invention is defined by the appended claims rather than by the description preceding them. All changes that fall within the metes and bounds of the claims, or equivalents of such metes and bounds, are therefore intended to be embraced by the claims.

What is claimed is:

1. A gas sensor comprising a cylindrical insulator having an element insertion hole extending from a proximal end to a distal end thereof, a gas sensing element airtightly fixed in said element insertion hole of the insulator, and a cylindrical housing having an inside space for placing said insulator, with an air side cover attached to a proximal end of said housing so as to confine an aerial atmosphere therein and a measured gas side cover attached to a distal end of said housing so as to confine a measured gas atmosphere therein, wherein a sealing material is provided within the cylindrical insulator at said proximal end of said element insertion hole for sealing a clearance between an inner surface of said element insertion hole and an outer surface of said gas sensing element, and a cushion filler is spaced apart from said sealing material at said distal end of said element insertion hole for sealing a clearance between an inner surface of said element insertion hole and the outer surface of said gas sensing element.

2. The gas sensor in accordance with claim 1, wherein a filling percentage of said cushion filler provided between said inner surface of said element insertion hole and the outer surface of said gas sensing element is in the range from 10% to 80%.

3. The gas sensor in accordance with claim 1, wherein an injection port is provided near an open edge of said element insertion hole at the distal end of said insulator for facilitating a filling operation of said sealing material or said cushion filler.

4. The gas sensor in accordance with claim 1, wherein said element insertion hole comprises a large-diameter portion and a smaller-diameter portion, and an inner diameter of said larger-diameter portion is larger than that of said smaller-diameter portion.

5. The gas sensor in accordance with claim 1, wherein said sealing material and/or said cushion filler is placed so as to fix at least two opposed surfaces of the inner surface of said element insertion hole and the outer surface of said gas sensing element.

6. A gas sensor comprising a cylindrical insulator having an element insertion hole extending from a proximal end to a distal end thereof, a gas sensing element airtightly fixed in said element insertion hole of the insulator, and a cylindrical housing having an inside space for placing said insulator, with an air side cover attached to a proximal end of said housing so as to confine an aerial atmosphere therein and a measured gas side cover attached to a distal end of said housing so as to confine a measured gas atmosphere therein, wherein a sealing material is provided within the cylindrical insulator at said proximal end of said element insertion hole for sealing a clearance between an inner surface of said element insertion hole and an outer surface of said gas sensing element, a cushion filler is spaced apart from said sealing material at said distal end of said element insertion hole for sealing a clearance between an inner surface of said element insertion hole and the outer surface of said gas sensing element, said insulator constitutes a main body and a separate body attached via a spacer to a distal end of said main body, so that said element insertion hole extends across both of said main body and said separate body, and said cushion filler is provided only in the element insertion hole of said separate body.

7. A gas sensor as claimed in claim 1, said cushion filler being capable of withstanding a loading force from 5N to 1,000N.

8. A gas sensor as claimed in claim 6, said cushion filler being capable of withstanding a loading force from 5N to 1,000N.

9. A gas sensor comprising:

a cylindrical insulator having an element insertion hole extending through its central region;

a gas sensing element disposed within the element insertion hole and being securely fixed at two spaced apart points of said element insertion hole within opposite ends of said cylindrical insulator to prevent said gas sensing element from swinging within said cylindrical insulator;

a sealing material provided at one of said two spaced apart points of said element insertion hole for securely fixing said gas sensing element to said cylindrical insulator and for sealing a clearance between an inner surface of said element insertion hole and an outer surface of said gas sensing element;

a cushion filler provided at the other end of said two spaced apart points of said element insertion hole for securely fixing said gas sensing element to said cylindrical insulator and for sealing a clearance between an inner surface of said element insertion hole and the outer surface of said gas sensing element;

an injection port provided near an open edge of said element insertion hole at the distal end of said insulator for facilitating a filling operation of said sealing material or said cushion filler; and a cylindrical housing having an inside space for receiving said cylindrical insulator and said gas sensing element, with an air side cover attached to a proximal end of said housing so as to confine an aerial atmosphere therein and a measured gas side cover attached to a distal end of said housing so as to confine a measured gas atmosphere therein.

10. A gas sensor as claimed in claim 9, wherein a filling percentage of said cushion filler provided between said inner surface of said element insertion hole and the outer surface of said gas sensing element is in the range from 10% to 80%.

11. The gas sensor in accordance with claim 9, wherein said element insertion hole comprises a large-diameter portion and a smaller-diameter portion, and an inner diameter of said larger-diameter portion is larger than that of said smaller-diameter portion.

12. A gas sensor comprising:

a cylindrical insulator having an element insertion hole extending through its central region;

a gas sensing element disposed within the element insertion hole and being securely fixed at two spaced apart points of said element insertion hole within opposite ends of said cylindrical insulator to prevent said gas sensing element from swinging within said cylindrical insulator;

a sealing material provided at one of said two spaced apart points of said element insertion hole for securely fixing said gas sensing element to said cylindrical insulator and for sealing a clearance between an inner surface of said element insertion hole and an outer surface of said gas sensing element;

a cushion filler provided at the other end of said two spaced apart points of said element insertion hole for securely fixing said gas sensing element to said cylindrical insulator and for sealing a clearance between an inner surface of said element insertion hole and the outer surface of said gas sensing element;

an injection port provided near an open edge of said element insertion hole at the distal end of said insulator for facilitating a filling operation of said sealing material or said cushion filler; and a cylindrical housing having an inside space for receiving said cylindrical insulator and said gas sensing element, with an air side cover attached to a proximal end of said housing so as to confine an aerial atmosphere therein and a measured gas side cover attached to a distal end of said housing so as to confine a measured gas atmosphere therein;

wherein said insulator constitutes a main body and a separate body attached via a spacer to a distal end of said main body, so that said element insertion hole extends across both of said main body and said separate body.

13. An improvement for a gas sensor having an elongated gas sensing element mounted within and extending through an elongated aperture of an insulating member, said elongated aperture having a first larger cross-section portion axially spaced from a second relatively smaller cross-section portion and wherein said gas sensing element is fixedly sealed in a gas-tight manner within said larger cross-section portion using a sealing material disposed within said larger cross-section portion, said improvement comprising:

a cushion material, softer than said sealing material, being disposed spaced apart from said sealing material within said smaller cross-section portion of the aperture and between the insulating member and the gas sensing element.

14. A method for protecting a gas sensor having an elongated gas sensing element mounted within and extending through an elongated aperture of an insulating member, said elongated aperture having a first larger cross-section portion axially spaced from a second relatively smaller cross-section portion and wherein said gas sensing element is fixedly sealed in a gas-tight manner within said larger cross-section portion using a sealing material, disposed within said larger cross-section portion said method comprising:

providing a cushion material, softer than said sealing material and spaced apart from said sealing material, within said smaller cross-section portion of the aperture and between the insulating member and the gas sensing element.

15. The gas sensor in accordance with claim 12, wherein said element insertion hole comprises a large-diameter portion and a smaller-diameter portion, and an inner diameter of said larger-diameter portion is larger than that of said smaller-diameter portion.

16. A gas sensor as claimed in claim 12, wherein a filling percentage of said cushion filler provided between said inner surface of said element insertion hole and the outer surface of said gas sensing element is in the range from 10% to 80%.

* * * * *